(12) United States Patent
Ito et al.

(10) Patent No.: US 9,933,370 B2
(45) Date of Patent: Apr. 3, 2018

(54) INSPECTION APPARATUS

(71) Applicant: HITACHI HIGH-TECHNOLOGIES CORPORATION, Tokyo (JP)

(72) Inventors: Masaaki Ito, Tokyo (JP); Hisashi Hatano, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 279 days.

(21) Appl. No.: 14/516,490

(22) Filed: Oct. 16, 2014

(65) Prior Publication Data

US 2015/0109435 A1 Apr. 23, 2015

(30) Foreign Application Priority Data

Oct. 17, 2013 (JP) ................................. 2013-215934

(51) Int. Cl.
*G06T 7/00* (2017.01)
*G01N 21/88* (2006.01)
*G01N 21/95* (2006.01)
*G01N 21/956* (2006.01)

(52) U.S. Cl.
CPC ..... *G01N 21/8803* (2013.01); *G01N 21/9501* (2013.01); *G01N 21/95607* (2013.01); *G06T 7/001* (2013.01); *G01N 21/8851* (2013.01); *G06T 2207/30148* (2013.01)

(58) Field of Classification Search
CPC .......... G06T 7/001; G06T 2207/30148; G01N 21/8803; G01N 21/95607; G01N 21/8851
See application file for complete search history.

(56) References Cited

U.S. PATENT DOCUMENTS

2007/0019858 A1 1/2007 Shimura
2007/0146707 A1* 6/2007 Matsumura ............ G01B 11/24
356/394

(Continued)

FOREIGN PATENT DOCUMENTS

JP 2007-033073 A 2/2007
JP 2010-043941 A 2/2010
JP 2011-008482 A 1/2011

OTHER PUBLICATIONS

M. Bohr et al., "Intel's Revolutionary 22nm Transistor Technology," May 2011, available at http://www.intel.com/content/www/us/en/silicon-innovations/revolutionary-22nm-transistor-technology-presentation.html, pp. 1-28.

(Continued)

*Primary Examiner* — Dave Czekaj
*Assistant Examiner* — Berteau Joisil
(74) *Attorney, Agent, or Firm* — Volpe and Koenig, P.C.

(57) ABSTRACT

When a size of a block on a wafer is equal to or smaller than an optical resolution of imaging optics, room for improvement in a signal-to-noise ratio has not been sufficiently considered in a conventional technique. One feature of the defect determination of the present invention is to include a filter processing for setting a predetermined partial area serving as a predetermined matrix for a first difference image, scanning the first difference image in the partial area, and outputting a second difference image, and a first threshold processing using a first threshold value for the second difference image. As a result, highly sensitive defect detection can be achieved.

7 Claims, 7 Drawing Sheets

(56) References Cited

U.S. PATENT DOCUMENTS

| | | | | |
|---|---|---|---|---|
| 2009/0175530 A1* | 7/2009 | Sjostrom | .............. | G01N 21/956 |
| | | | | 382/152 |
| 2011/0188734 A1* | 8/2011 | Tsuchiya | ............... | G06T 7/0002 |
| | | | | 382/149 |
| 2013/0027751 A1* | 1/2013 | Uchidate | .............. | H04N 1/4074 |
| | | | | 358/3.03 |

OTHER PUBLICATIONS

Japanese Office Action dated Apr. 18, 2017 issued in Japanese Patent Application No. 2013-215934, with English translation.

* cited by examiner

SCANNING OF PARTIAL REGION FOR EACH PIXEL

| 0 | 0 | 0 | 1 | 2 | 1 | 0 | 0 | 0 |
|---|---|---|---|---|---|---|---|---|
| 0 | 0 | 0 | 1 | 1 | 1 | 0 | 0 | 0 |
| 0 | 0 | 0 | 0 | -1 | 0 | 0 | 0 | 0 |
| 0 | 0 | 0 | -10 | -15 | -10 | 0 | 0 | 0 |
| 0 | 1 | 0 | 1 | 9 | 1 | 0 | 1 | 0 |
| 0 | 1 | 1 | 5 | 15 | 5 | 1 | 1 | 0 |
| 0 | 0 | 0 | 2 | 4 | 2 | 0 | 0 | 0 |
| 0 | 0 | 0 | 2 | 2 | 2 | 0 | 0 | 0 |
| 0 | 0 | 0 | 1 | 1 | 1 | 0 | 0 | 0 |

PARTIAL AREA
CENTER POSITION OF PARTIAL AREA

FIG. 6

| 0 | 0 | 0 | 1 | 2 | 1 | 0 | 0 | 0 |
|---|---|---|---|---|---|---|---|---|
| 0 | 0 | 0 | 3 | 3 | 3 | 0 | 0 | 0 |
| 0 | 0 | 11 | 16 | 16 | 16 | 11 | 0 | 0 |
| 0 | 0 | 11 | 24 | 24 | 24 | 11 | 0 | 0 |
| 0 | 1 | 15 | 30 | 30 | 30 | 15 | 1 | 0 |
| 0 | 1 | 1 | 5 | 15 | 5 | 1 | 1 | 0 |
| 0 | 0 | 0 | 2 | 4 | 2 | 0 | 0 | 0 |
| 0 | 0 | 0 | 2 | 2 | 2 | 0 | 0 | 0 |
| 0 | 0 | 0 | 1 | 1 | 1 | 0 | 0 | 0 |

PARTIAL AREA
CENTER POSITION OF PARTIAL AREA

INSPECTION APPARATUS

CROSS-REFERENCE TO RELATED APPLICATION

The present application claims priority from Japanese Patent Application No. 2013-215934 filed on Oct. 17, 2013, the content of which is hereby incorporated by reference into this application.

TECHNICAL FIELD OF THE INVENTION

The present invention relates to a defect inspection apparatus for a sample having a pattern formed therein, such as a wafer in manufacture of a semiconductor device. More particularly, the present invention relates to image processing in an optical defect inspection apparatus.

BACKGROUND OF THE INVENTION

In processes for manufacturing a semiconductor device, film formation by a sputtering method or a chemical vapor deposition method, planarization by a chemical mechanical polishing method, and patterning by a lithography method and an etching method are repeated a large number of times. In order to ensure a yield of the semiconductor device, a wafer is extracted in the middle of the manufacturing processes, and is subjected to defect inspection. Defects include contaminant particles on a surface of the wafer, and scratch thereon, and pattern defects thereon (a short circuit, an open circuit, etc.). A preferred aim of the defect inspection is to manage a state of a manufacturing apparatus and specify a process in which a defect has occurred and a cause of the defect.

An optical defect inspection apparatus that irradiates a wafer with light to acquire an image has a higher throughput than a defect inspection apparatus of another type such as an electron beam type, and therefore, is frequently used for inline inspection. As a semiconductor device is miniaturized, defect size to be detected decreases, improvement in detection sensitivity is required.

In the wafer, hundreds of devices (referred to as chips) having the same pattern as each other are formed with a constant pitch. Also, in a memory unit of the device or others, a large number of cells having the same pattern as each other are formed with a short pitch. In the optical defect inspection apparatus, a method of detecting the defect by comparing images between the chips or between cells is used.

A specific defect detection method is disclosed in, for example, Japanese Patent Application Laid-Open Publication No. 2007-33073 (Patent Document 1). In chip comparison, positions of two images (an inspection image and a reference image) of the chips which are adjacent to each other are aligned, and then, a difference between them is obtained. In cell comparison, positions of two images of cells which are separated from each other by an integral multiple of a repetitive pitch are aligned, and then, a difference between them is obtained. In the obtained difference image, a position having a pixel value larger than a threshold value is determined to be the defect. Here, the threshold value is set so as to detect a real defect and not to detect a false defect caused by variation (noise) in the pixel value as much as possible. Therefore, in order to improve the detection sensitivity, it is important to enhance a signal-to-noise ratio of the difference image.

Also, Japanese Patent Application Laid-Open Publication No. 2011-8482 (Patent Document 2) discloses that the pixel value of the difference image has a positive value or a negative value depending on cases in the defect inspection apparatus using the image comparison.

Figure 9:
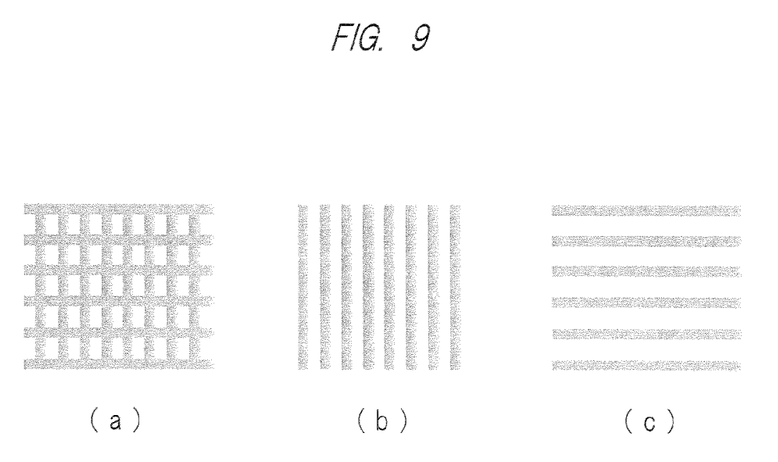
FIG. 9 is a diagram illustrating an example of a pattern in a gate process of a transistor.

Note that a configuration illustrated in FIG. 9 described later has been described in a document, Mark Bohr, Kaizad Mistry, "Intel's Revolutionary 22 nm Transistor Technology", p. 8, [online] May 2011, [retrieved on 2013 24 Sep.], Retrieved from the internet <URL:http://www.intel.com/content/www/us/en/silicon-innovations/revolutionary-22nm-transistor-technology-presentation.html> (Non-Patent Document 1).

SUMMARY OF THE INVENTION

In the defect detection method disclosed in Patent Document 1, a position of the difference image where the pixel value is larger than the threshold value is determined as the defect. That is, a state that the pixel value is the positive value at the defect position of the difference image or in the vicinity of the defect position is an implicit assumption.

Also, in the defect detection method disclosed in Patent Document 2, a position of the difference image where the positive pixel value is larger than a positive threshold value is determined as a bright defect, and a position thereof where the negative pixel value is smaller than a negative threshold value is determined as a dark defect. Here, a state that the bright defect and the dark defect are of different types from each other is an implicit assumption.

Incidentally, the pattern in the wafer is various. In a gate process of a transistor that has been miniaturized, a pattern as illustrated in an item (a) of FIG. 9 is formed (Non-patent Document 1). This pattern is formed separately by two steps in consideration of a resolution limit of a lithographic technique. That is, a line pattern in one direction is formed as illustrated in an item (b) of FIG. 9, and then, a line pattern in a direction perpendicular to the above-described direction is formed as illustrated in an item (c) of FIG. 9. Each of the patterns (b) and (c) to be inspected has such a feature that a plurality of line patterns are collected to form a block shape. In such a block-shaped pattern, the positive pixel value and the negative pixel value are mixed at the defect position of the difference image or in the vicinity of the defect position thereof in some cases. In the present invention, it has been found out that the phenomenon is caused often when a size of a predetermined block on the wafer is substantially equal to or smaller than an optical resolution of an imaging optics.

In this case, in a conventional defect detection method, only the positive pixel value or only the negative pixel value is compared with the threshold value, and therefore, defect signals cannot be sufficiently used. That is, the conventional technique does not consider that the signal-to-noise ratio of the difference image is low. More specifically, the conventional technique does not sufficiently consider that there is room for improvement in the signal-to-noise ratio when the size of the block on the wafer is equal to or smaller than the optical resolution of the imaging optics.

A preferred aim of the present invention is to provide a defect inspection apparatus including a defect detection method with a high signal-to-noise ratio when a positive pixel value and a negative pixel value are mixed at a defect position of a difference image or in vicinity of the defect position.

One feature of the present invention is that an inspection apparatus includes: an illumination optics that supplies light to a sample having a predetermined block formed therein; an imaging optics that detects the light from the sample; and a processing unit. The processing unit obtains a first difference image from images generated by the imaging optics, and performs first defect determination for the first difference image for a case that the size of the block is equal to or smaller than the optical resolution of the imaging optics.

More specifically, the present invention has one feature that the first defect determination includes: a filter process for setting a predetermined partial area in the first difference image which is a predetermined matrix, scanning the first difference image in the partial area, and outputting a second difference image; and a first threshold process for using a first threshold value for the second difference image.

According to the present invention, defect detection with a high sensitivity is achieved. For example, when a positive pixel value and a negative pixel value are mixed at a defect position of a difference image or in vicinity of the defect position, a defect signal is emphasized, and therefore, defect detection with a high signal-to-noise ratio is achieved.

DESCRIPTIONS OF THE PREFERRED EMBODIMENTS

Hereinafter, an embodiment of the present invention will be described by using the drawings.

Figure 1:
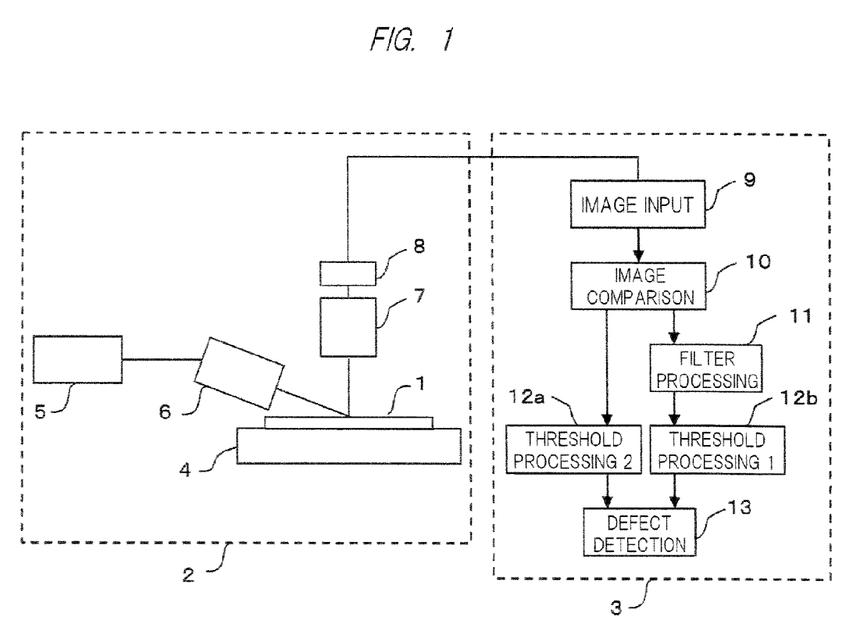
FIG. 1 is a diagram illustrating an embodiment of a defect inspection apparatus according to the present invention.

FIG. 1 illustrates a schematic configuration of a defect inspection apparatus according to the present invention. An inspection target is a semiconductor wafer (hereinafter, referred to as a wafer 1) including a plurality of chips each having a pattern formed therein.

The defect inspection apparatus is roughly separated into an image acquisition system 2 and an image processing system 3. The image acquisition system 2 includes a stage 4, a light source 5, an illumination optics 6, an imaging optics 7, and an image sensor 8.

The stage 4 loads the wafer 1 thereon, and moves in X-, Y-, and Z-directions and rotates in a θ direction (around a Z-axis). Here, the X-direction and the Y-direction are in-plane directions of the wafer 1, and the Z-direction is a normal direction to the wafer 1.

As the light source 5, a coherent light source such as a laser, an incoherent light source such as a discharge lamp, or others is used. A wavelength region includes visible light, ultraviolet light, deep ultraviolet light, vacuum ultraviolet light, and others.

The illumination optics 6 adjusts light emitted from the light source 5 so as to have a predetermined wavelength, polarization, power, a beam size, and others, and causes the adjusted light to enter the wafer 1. An illumination region formed on the wafer 1 is a substantial line or spot in some cases.

The scattered light from the wafer 1 is collected by a dark field imaging optics 7. Here, specular light from the wafer 1 is emitted to outside an aperture of the imaging optics 7. As the imaging optics 7, a refractive type formed of lenses, a reflective type formed of mirrors, a catadioptric type in combination of mirrors and lenses, and a diffractive type of Fresnel zone plates or others are used. A spatial filter for shielding unnecessary light from the wafer 1 is arranged on a Fourier plane of the imaging optics 7 in some cases.

A dark field image of the wafer 1 is enlarged and formed on the image sensor 8. As the image sensor 8, an area sensor such as a CCD sensor or a line sensor such as a time delay integration (TDI) sensor is used.

An inspection image captured by the image sensor 8 is converted into a digital signal by an A/D converter (not illustrated). The stage 4 is scanned in the X-direction and the Y-direction in parallel with the above-described operation. As described above, the image of the chip to be inspected is sequentially transmitted to the image processing system 3. The stage 4 is further scanned so that the image of the predetermined chip on the wafer 1 is sequentially transmitted to the image processing system 3.

The image processing system 3 includes an image input unit 9, an image comparison unit 10, a filter unit 11, a first threshold processing unit 12b, a second threshold processing unit 12a, and a defect detection unit 13.

The image input unit 9 reads the image of the chip to be inspected and a reference image having the same pattern as the one being acquired in a different chip. The image comparison unit 10 performs positioning alignment of the inspection image and the reference image, and then, outputs a difference between them (hereinafter, referred to as a first difference image).

On the other hand, the filter unit 11 performs a filter processing to the first difference image for each predetermined partial area, and outputs a second difference image. The filter processing will be described in detail later.

The first threshold processing unit 12b compares a pixel value of the second difference image with a previously-set first threshold value, and determines the pixel as a defect if the pixel value is larger than the threshold value. Here, usually, the first threshold value is set to be larger than a second threshold value described below. This is because a background noise of the second difference image is larger than a background noise of the first difference image in some cases.

The second threshold processing unit 12a compares a pixel value of the first difference image with the previously-set second threshold value, and determines the pixel as a defect if the pixel value is larger than the threshold value. When the pixel value is negative, note that the pixel is determined as the defect if the pixel value is smaller than the threshold value (negative).

The defect detection unit 13 takes a logical sum (can also be expressed as "or") of a determination result of the first threshold processing unit and a determination result of the second threshold processing unit, and outputs the logical sum as a defect of the inspection image if at least one of the determination results shows the defect.

In this manner, after the predetermined chip on the wafer is inspected, a defect map within a wafer plane is outputted to a user interface unit (not illustrated).

Figure 2:
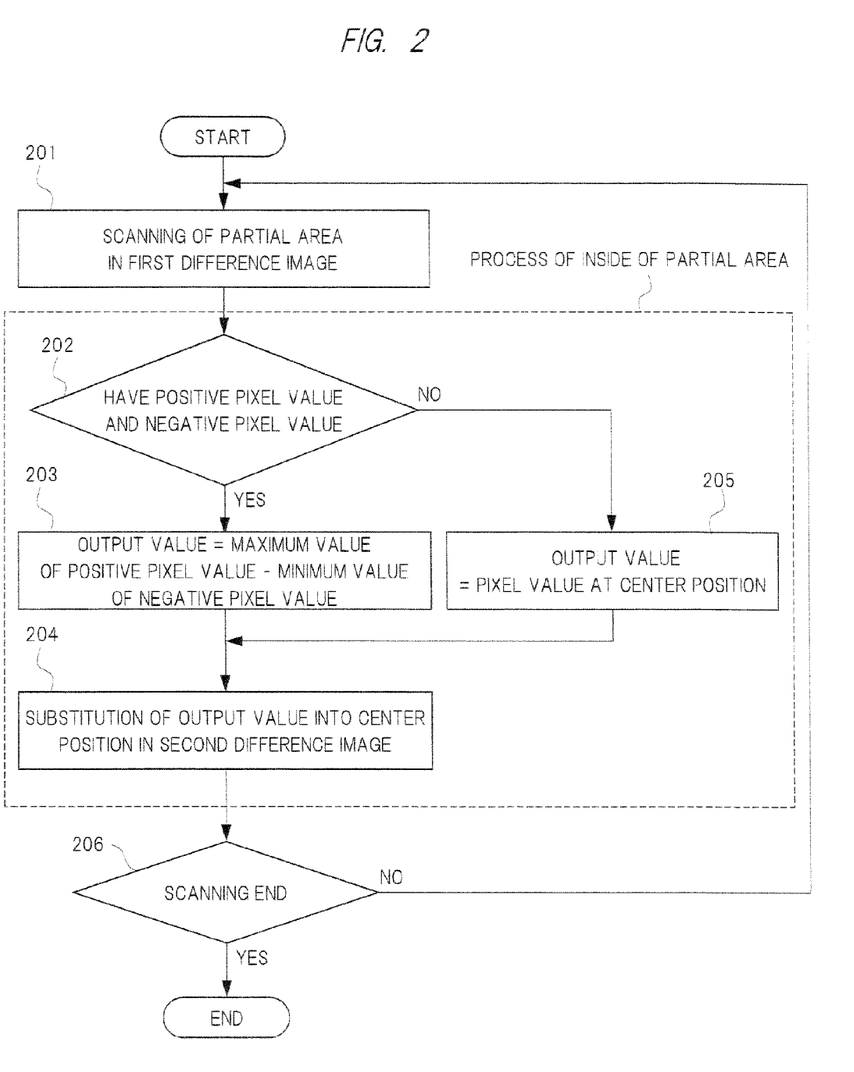
FIG. 2 is a diagram illustrating a flow of a filter process according to the present invention.

Next, details of the filter processing for the first difference image performed by the filter unit 11 will be described with reference to FIG. 2. The difference image is numerical data in a matrix format, and the filter processing corresponds to a so-called neighborhood operation.

First, in step 201, the filter unit 11 sets a predetermined partial area in the first difference image, and scans the first difference image in the partial area.

The partial area is a predetermined matrix such as a "3×3 matrix". If the pixel value of the partial area does not exist in the vicinity of the boundary of the difference image, note that 0 is embedded into this pixel. That is, if the partial area partially exists outside the first difference image, the filter unit 11 handles the part as invalid.

Also, if the number of pixels in each of a row direction and a column direction of the partial area is even, an index of a center position of the partial area described below is determined by dividing the number of pixels by 2, followed by rounding-up or rounding-down that number.

Next, in step S202, the filter unit 11 determines whether the partial area has positive pixel values and negative pixel values.

If the determination is true (YES), the flow proceeds to step S203 so that the filter unit 11 takes a difference value "MAX-MIN" between a maximum value MAX of the positive pixel values and a minimum value MIN of the negative pixel values as an output value.

On the other hand, if the determination is false (NO), the flow proceeds to step S205 so that a pixel value CEN at the center position of the partial area is taken as the output value. And, in step S204, either one of the above-described output values, that is, "MAX-MIN" or "CEN" is substituted into the center position of the partial area in the second difference image.

In this manner, the partial area in the first difference image is scanned while the processing is performed for each of the partial areas. And, if a sum set of the scanned partial areas matches an area of the first difference image, the filter processing ends.

For the above-described scanning, the center position of the partial area may be scanned for all the pixels of the first difference image. That is, the center position of the partial area may be moved by each one pixel. In this case, detection sensitivity is stabilized even if the defect is at any position of the first difference image.

Also, as long as the sum set of the scanned partial areas matches the area of the first difference image, the center position of the partial area is not always scanned for all the pixels of the first difference image. That is, the center position of the partial area may be moved by each two pixels, or may be moved by the same number of pixels as that of the partial area. In this case, while the stability of the detection sensitivity is slightly lower, a calculation amount of the filter processing can be reduced.

Next, emphasis of the defect signal of the pattern by the filter processing of the first difference image will be described.

Figures 3, 4:
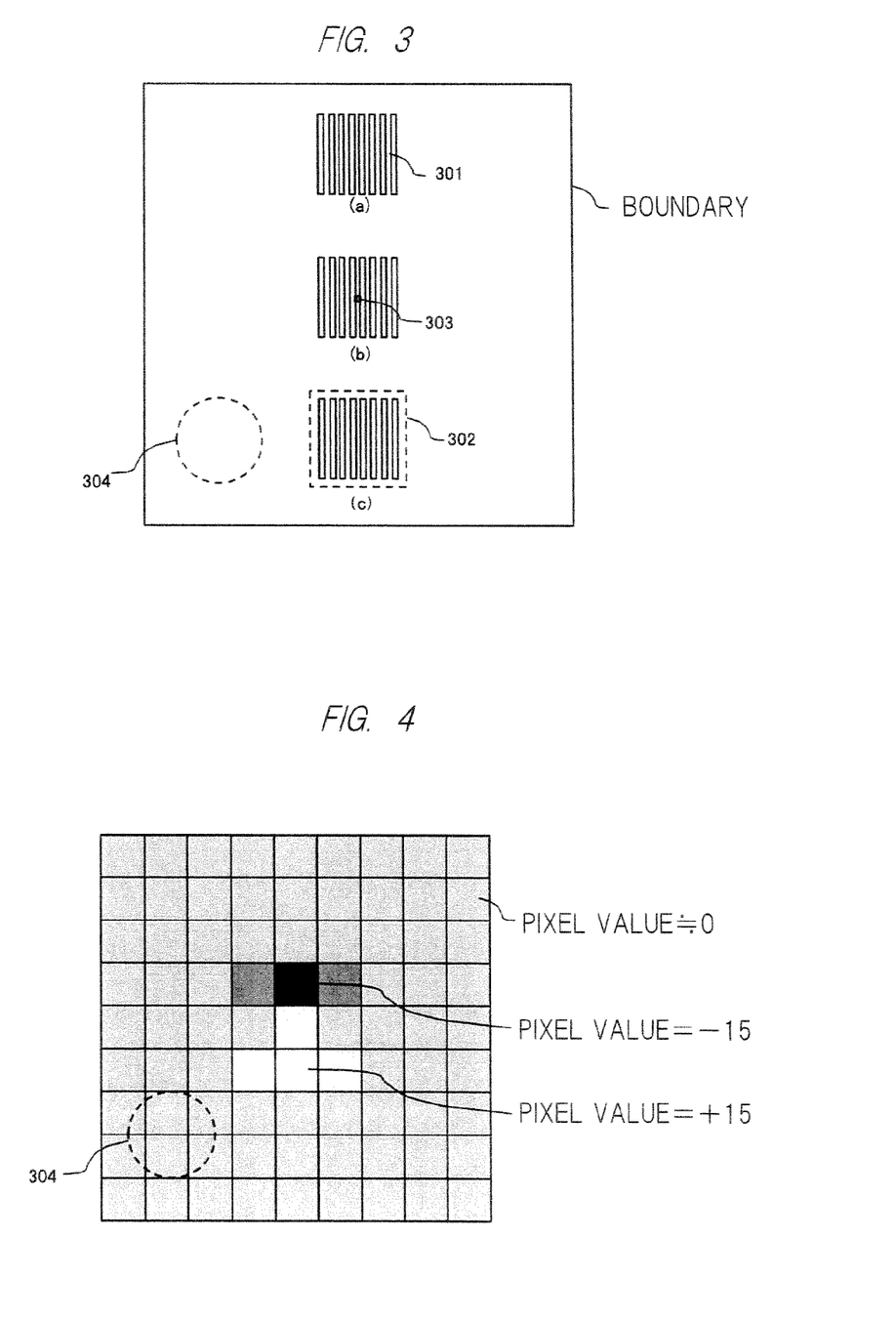
FIG. 3 is a diagram illustrating an example of a pattern to be inspected.
FIG. 4 is a diagram illustrating a first difference image by a gray scale.

FIG. 3 illustrates an example of the pattern to be inspected on the wafer 1. On the wafer 1, as illustrated in an item (a) of FIG. 3, a large number of line patterns 301 are arranged, and a plurality of sets (referred to as a block 302) of the line patterns 301 exist. Here, a size of the block 302 is similar to the optical resolution (indicated by 304) of the imaging optics 7. In an item (b) of FIG. 3, in the one block 302, the line patterns are partially connected to each other. This connection is handled as a defect 303.

FIG. 4 illustrates the first difference image to be inspected on a gray scale in 9×9 pixels. Note that the reference image is an image acquired in the chip having no defect. Also, the optical resolution 304 corresponds to about two pixels. The difference image has such a feature that the positive pixel values and the negative pixel values are mixed in the vicinity of the defect position. The maximum value of the positive pixel values is "+15", and the minimum value of the negative pixel values is "−15". Both their absolute values are the same as each other. That is, when threshold processing is performed for the first difference image, the defect signal is 15.

A reason why the positive pixel values and the negative pixel values are mixed in the vicinity of the defect position as described above is that scattered light from the defect and scattered light from an edge of the block etc. interfere with each other on an image plane so that an intensity distribution of an optical image occurs. If the size of the block is close to the optical resolution, the above-described phenomenon may occur although depending on a position of the defect in the block.

Figure 5:
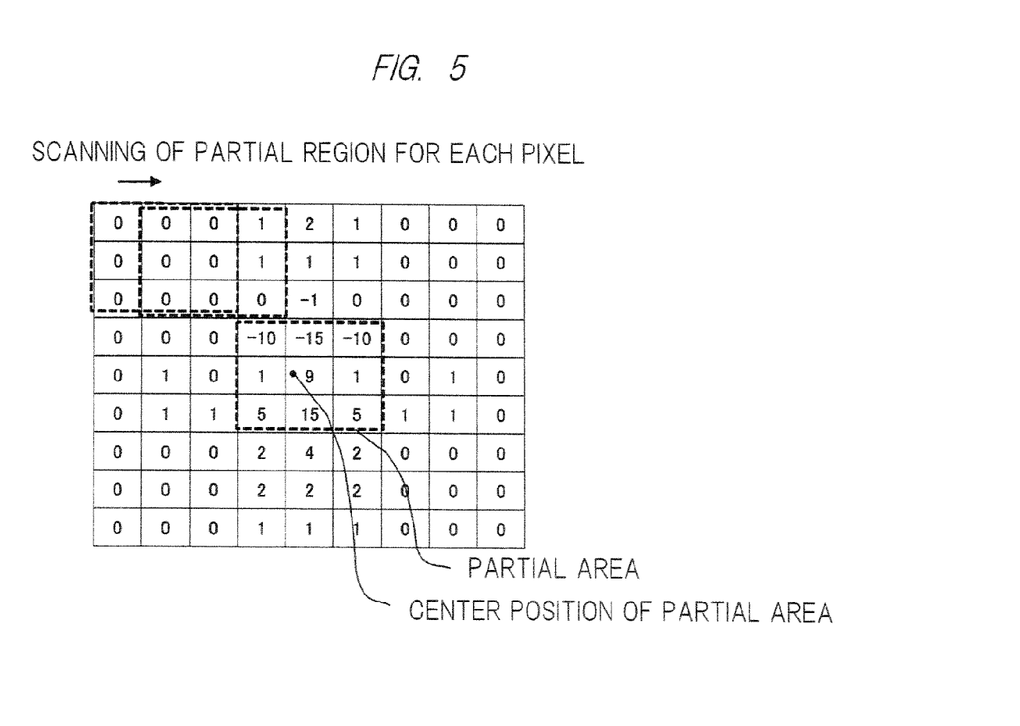
FIG. 5 is a diagram illustrating numerical data of the first difference image.

FIG. 5 illustrates an example of the numerical data of the first difference image. Here, the size of the partial area in the filter processing is set to the sum of the optical resolution and the pixel size as a physical size. That is, the size of the partial area is set to "3×3" pixels (a frame indicated by a broken line) as a matrix. And, the filter processing is performed while scanning the partial area in each one pixel, and the second difference image is outputted.

Figure 6:
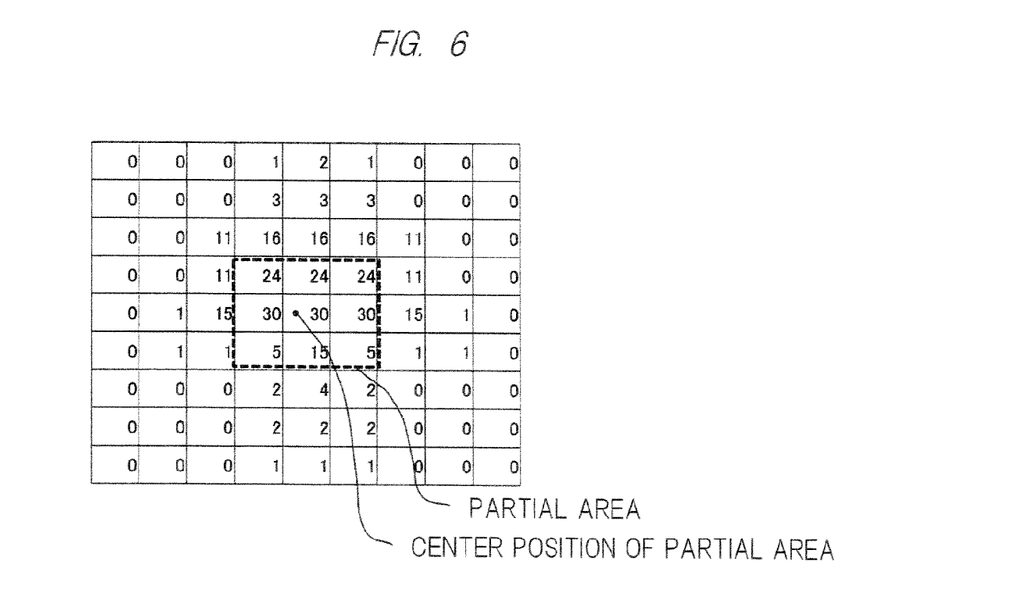
FIG. 6 is a diagram illustrating numerical data of a second difference image.
Figure 7:
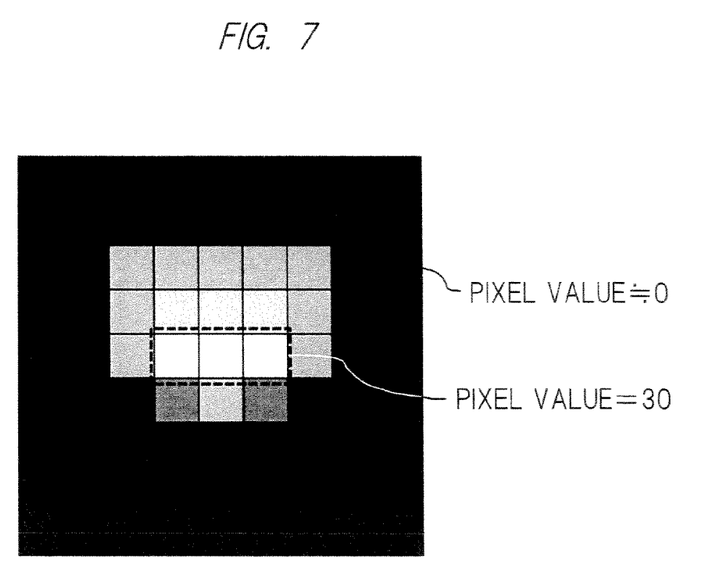
FIG. 7 is a diagram illustrating the second difference image by a gray scale.

FIG. 6 illustrates numerical data of the second difference image. Also, FIG. 7 illustrates the second difference image on a gray scale. In the vicinity of the defect position, the maximum value of the pixel values is 30. That is, when the threshold processing is performed for the second difference image, the defect signal is 30, and is emphasized to be twice larger than the first difference image.

Incidentally, the second difference image has a plurality of the maximum values of the pixels. That is, the plurality of pixels which are defect candidates exist. By selecting the pixel at the center of the plurality of pixels, a determination result close to a true defect position is obtained.

Although omitted in the foregoing description, the first difference image contains a background noise caused by a variation in the pattern shape and others. The background noise is increased by the above-described filter processing, and therefore, it is usually required to set the first threshold value to be larger than the second threshold value.

Figure 8:
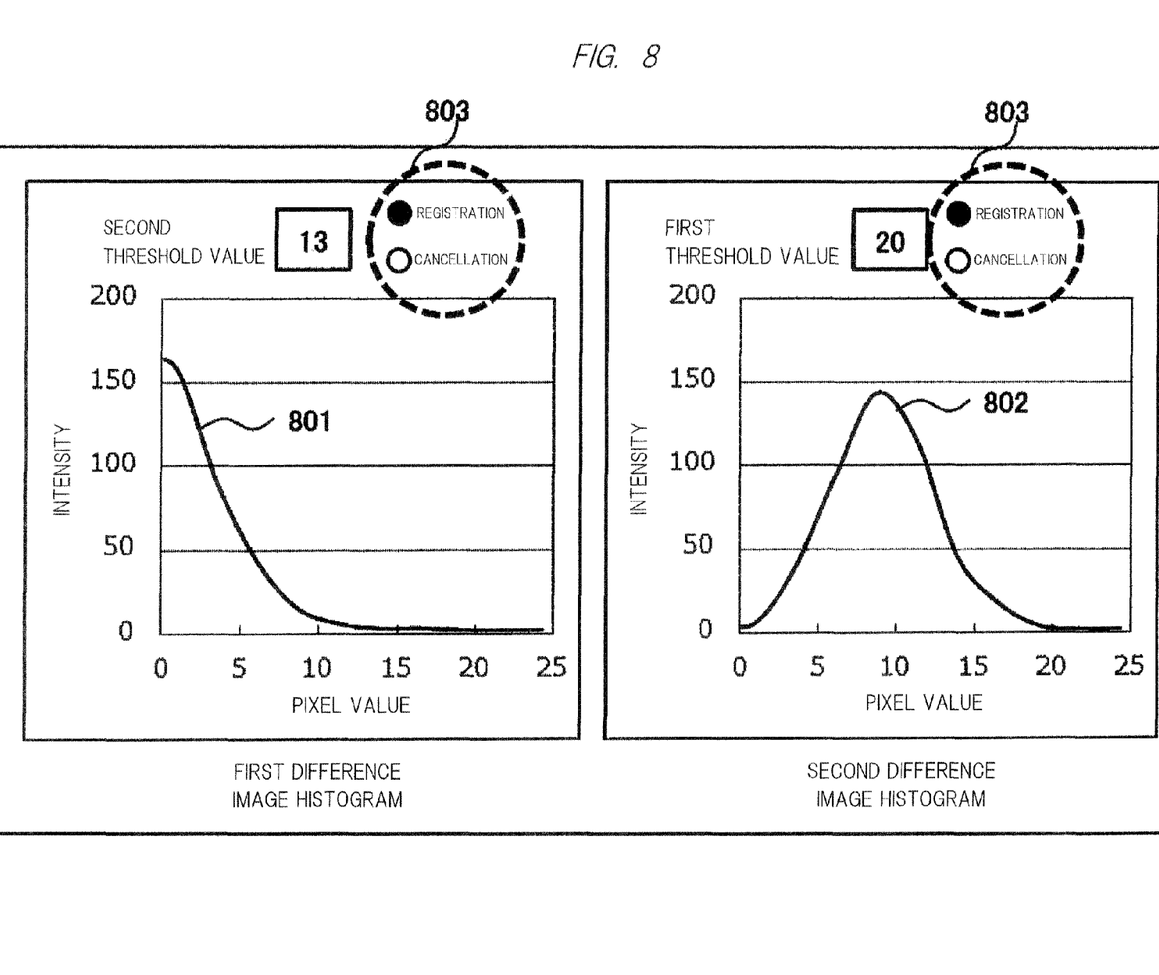
FIG. 8 is a diagram illustrating a user interface screen for setting a threshold.

FIG. 8 illustrates a user interface screen for setting the threshold values. Histograms 801 and 802 are displayed for the first difference image and the second difference image, respectively. A user refers to each of the histograms 801 and 802, and sets pixel values having sufficiently small frequencies to the first threshold value and the second threshold value. The threshold value is registered by checking "register" in a check box 803. In FIG. 8, "13" and "20" are registered as the second threshold value and the first threshold value, respectively.

In the pattern as described above, the second difference image has a larger increase rate of the defect signal which exceeds an increase rate of the threshold value than the first difference image. That is, a higher detection sensitivity is obtained by performing the threshold processing to the second difference image. On the other hand, if the size of the block is larger (more specifically, sufficiently larger) and the line pattern is significantly longer than those of the optical resolution of the imaging optics 7, the pixel values are only positive at the defect position of the first difference image or in the vicinity of the defect position. In this case, the second difference image is the same as the first difference image in the defect signal but is larger than the same in the threshold value, and therefore, is lower in the detection sensitivity. That is, a higher detection sensitivity is obtained by performing the threshold processing to the first difference image.

The defect determination performed by the second threshold processing unit 12a can be interpreted as a suitable processing for (1) a case of a sufficiently large block size and a very long line pattern than those of the optical resolution of the imaging optics 7. On the other hand, the defect determination performed by the first threshold processing unit 12b can be interpreted as a suitable processing for (2) a case that the size of the block is substantially the same as or substantially smaller than the optical resolution of the imaging optics 7. One idea of the present embodiment is that the defect can be detected with high sensitivity even in both of the case (1) and the case (2) by obtaining a logical sum of results of the two defect determinations.

In the present embodiment, the defect determination by using the first difference image and the defect determination by using the second difference image are compensated for each other, and therefore, high detection sensitivity is obtained for a wide variety of patterns.

While a dark field defect inspection apparatus taking a semiconductor wafer as a target has been described in the above-described present embodiment. However, the present invention is also applicable to a bright field defect inspection apparatus that detects specular light from a wafer.

Further, the arrangement of the imaging optics 7 is not limited to that in the present embodiment. If an optical axis of the imaging optics 7 and a normal line of the wafer 1 form a predetermined angle with each other, a case that oblique detection is performed as another interpretation is also within the scope of the disclosure of the present specification. Also, a plurality of imaging optics 7 may be arranged. An operator may optionally determine which of the plurality of imaging optics 7 performs the defect determination in the present embodiment.

Also, the present invention is widely applicable to a sample on which a pattern such as a magnetic storage medium or a liquid crystal device is formed.

What is claimed is:

1. An inspection apparatus comprising:
an illumination optics that supplies light to a sample having a predetermined block formed therein;
an imaging optics that detects light from the sample; and
a processor,
wherein the processor obtains a first difference image from an image generated by the imaging optics, and performs first defect determination to the first difference image for a case that a size of the block is substantially equal to or smaller than an optical resolution of the imaging optics,
wherein the first defect determination includes:
a filter processing for setting a predetermined partial area serving as a predetermined matrix for the first difference image, scanning the first difference image in the partial area, and outputting a second difference image; and
a first threshold processing using a first threshold value for the second difference image,
wherein the filter processing includes a determination processing for determining whether the partial area has positive pixel values and negative pixel values or not, and
wherein, when a result of the determination processing is true, the filter processing takes a difference value between a maximum value of the positive pixel values and a minimum value of the negative pixel values as an output value, and a maximum value of the output value is greater than a maximum pixel value of the positive pixel values and absolute values of the negative pixel values.

2. The inspection apparatus according to claim 1, wherein the processor performs second defect determination to the first difference image for a case that the size of the block is substantially larger than the optical resolution of the imaging optics.

3. The inspection apparatus according to claim 2, wherein the processor obtains a logical sum of a result of the first defect determination and a result of the second defect determination.

4. The inspection apparatus according to claim 3, wherein the second defect determination includes a second threshold processing using a second threshold value for the first difference image, and
the first threshold value is larger than the second threshold value.

5. The inspection apparatus according to claim 1, wherein, when the result of the determination processing is false, the filter processing takes a pixel value at a center position of the partial area as the output value.

6. The inspection apparatus according to claim 1, wherein the processing unit performs second defect determination to the first difference image for a case that the size of the block is substantially larger than the optical resolution of the imaging optics.

7. The inspection apparatus according to claim 6, wherein the processing unit obtains a logical sum of a result of the first defect determination and a result of the second defect determination.

* * * * *